United States Patent
Kim et al.

(10) Patent No.: US 11,821,045 B2
(45) Date of Patent: Nov. 21, 2023

(54) COLORECTAL CANCER-SPECIFIC METHYLATION BIOMARKERS FOR DIAGNOSING COLORECTAL CANCER

(71) Applicants: GENINUS INC., Seoul (KR); SAMSUNG LIFE PUBLIC WELFARE FOUNDATION, Seoul (KR)

(72) Inventors: Jinho Kim, Seoul (KR); Woong Yang Park, Seoul (KR); Yong Beom Cho, Seongnam-si (KR); Ga Hyun Kim, Seoul (KR); Jun Gi Jeong, Seoul (KR); Dong Hyun Park, Seoul (KR)

(73) Assignees: GENINUS INC., Seoul (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 71 days.

(21) Appl. No.: 17/228,940

(22) Filed: Apr. 13, 2021

(65) Prior Publication Data
US 2022/0325349 A1    Oct. 13, 2022

(51) Int. Cl.
*C12Q 1/6886*    (2018.01)

(52) U.S. Cl.
CPC ..... *C12Q 1/6886* (2013.01); *C12Q 2600/154* (2013.01)

(58) Field of Classification Search
CPC ............. C12Q 1/6886; C12Q 2600/154
See application file for complete search history.

(56) References Cited

U.S. PATENT DOCUMENTS

| 2014/0274748 A1 | 9/2014 | Ahlquist et al. |
| 2015/0292023 A1 | 10/2015 | Fishel et al. |
| 2018/0245157 A1 | 8/2018 | Allawi et al. |

FOREIGN PATENT DOCUMENTS

| EP | 2 749 642 | 7/2014 |
| KR | 10-1860238 | 5/2018 |
| WO | WO 2005/001141 | 1/2005 |
| WO | WO 2013/097868 | 7/2013 |
| WO | WO 2018/087129 A1 | 5/2018 |

OTHER PUBLICATIONS

W. Poole et al. "Combining dependent P-values with an empirical adaptation of Brown's method" Bioinformatics. 32, 2016. i431H436.

*Primary Examiner* — Sarae L Bausch
(74) *Attorney, Agent, or Firm* — Oblon, McClelland, Maier & Neustadt, L.L.P.

(57) ABSTRACT

Provided is a colorectal cancer-specific methylation biomarker for diagnosing colorectal cancer. Since a gene marker according to an embodiment exhibits a specific methylation pattern in colorectal cancer tissue, it can be usefully used as a methylation marker for diagnosing colorectal cancer, thereby increasing the cure rate of colorectal cancer by early diagnosis and treatment of colorectal cancer.

4 Claims, No Drawings

COLORECTAL CANCER-SPECIFIC METHYLATION BIOMARKERS FOR DIAGNOSING COLORECTAL CANCER

BACKGROUND

1. Field

One or more embodiments relate to colorectal cancer-specific methylation biomarkers for diagnosing colorectal cancer.

2. Description of the Related Art

DNA methylation mainly occurs in cytosines of CpG islands located in promoter regions of a particular gene and interrupts binding of a transcription factor, thereby causing gene silencing in which expression of the gene is blocked, and is a major mechanism by which the function of the gene is lost without mutation in a coding sequence. In addition to the promoter regions of the gene, DNA methylation in non-translation regions such as enhancers and regulatory regions is also known to act as a causative mechanism of various diseases together with structural modification of chromosomes and histone modification. In various diseases including cancer, such abnormal methylation/demethylation in CpG islands has been reported, and various attempts have been made to examine the methylation of promotors of disease-related genes and use them for diagnosing various diseases (Korean Patent No. 10-1860238).

Meanwhile, genes exhibiting a colorectal cancer-specific methylation pattern may be used as markers for diagnosing colorectal cancer. However, only a few methylation marker genes such as SEPT9 have bene identified for colorectal cancer so far. Therefore, there is a need for more methylation marker genes to diagnose colorectal cancer with higher sensitivity.

SUMMARY

An aspect provides a composition for diagnosing colorectal cancer comprising an agent capable of measuring a methylation level of at least one gene selected from the group consisting of CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B.

Another aspect provides a kit for diagnosing colorectal cancer comprising the composition.

Another aspect provides a method of diagnosing colorectal cancer in a subject, the method comprising: measuring a methylation level of at least one gene selected from the group consisting of CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B in a biological sample obtained from the subject; and comparing the measured methylation level of the gene with a methylation level of a normal control.

Additional aspects will be set forth in part in the description which follows and, in part, will be apparent from the description, or may be learned by practice of the presented embodiments of the disclosure.

An aspect provides a composition for diagnosing colorectal cancer comprising an agent capable of measuring a methylation level of at least one gene selected from the group consisting of CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B.

The term "methylation" may refer to addition of a methyl group to a base causing a change in an expression pattern of a gene. In one embodiment, the methylation may occur in cytosines of CpG islands where CpG, in which C and G bases are consecutively present, is concentrated in the nucleotide sequence of the CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B genes, thereby inhibiting the binding of transcription factors and blocking the expression of a particular gene. In DNAs of mammalian cells, in addition to adenine, cytosine, guanine, and thymine, there is a base called 5-methylcytosine (5-mC) in which a methyl group is linked to a $5^{th}$ carbon of a cytosine ring. Methylation of the 5-methylcytosine occurs only at C of CG dinucleotide (5'-mCG-3') called CpG, and methylation of CpG suppresses expression of transposon and genome repeats. In addition, since the 5-mC of CpG tends to be naturally deaminated to be converted into thymine (T), CpG is a site where most epigenetic changes occur frequently in mammalian cells. In addition, when methylation occurs, the binding of transcription factors is disturbed, and the expression of a particular gene is suppressed. On the contrary, when non-methylation or hypomethylation occurs, the expression of a particular gene is increased.

The term "CpG island" refers to a genomic region in which CpGs are gathered at an exceptionally high frequency, and has a length of 0.2 kb to 3 kb in which a C+G content is 50% or more, and a CpG ratio is 3.75% or more. In the CpG, C represents cytosine, G represents guanine, and p may refer to a phosphodiester bond between cytosine and guanine. There are about 45,000 CpG islands in the human genome, most of which are found in promoter regions that control gene expression. In fact, the CpG islands are found in promoters of housekeeping genes, which account for about 50% of human genes. In somatic cells of normal humans, the CpG islands of the promoter region of the housekeeping gene are unmethylated, and genes not expressed during a development, such as imprinted genes and genes on inactivated X chromosome, are methylated.

The term "measuring a methylation level" may refer to measuring the degree of methylation in a nucleotide sequence, specifically, measuring an amount of methylation present in a DNA sequence of a target DNA methylation gene in all genomic regions and some non-genomic regions.

In an embodiment, the methylation level of the CpG site of the gene may be increased, i.e., hyper-methylated, in colorectal cancer tissue compared to normal tissue.

In an embodiment, the measuring of the methylation level of the gene is performed by measuring a methylation level of a CpG site of: a sequence from 65589615 to 65629481 of chromosome #11 (Genbank Accession No. NC_000011.9) for the CFL1 (cofilin 1) gene; a sequence from 62102663 to 62661012 of chromosome #12 (Genbank Accession No. NC_000012.11) for the FAM19A2 (TAFA chemokine like family member 2) gene; a sequence from 41098689 to 41135467 of chromosome #19 (Genbank Accession No. NC_000019.10) for the LTBP4 (latent transforming growth factor beta binding protein 4) gene; a sequence from 17270300 to 17277761 of chromosome #10 (Genbank Accession No. NC_000010.10) for the VIM (vimentin) gene; a sequence from 44870219 to 45117290 of chromosome #1 (Genbank Accession No. NC_000001.10) for the RNF220 (ring finger protein 220) gene, a sequence from 73331531 to 73907779 of chromosome #6 (Genbank Accession No. NC_000006.11) for the KCNQ5 (potassium voltage-gated channel subfamily Q member 5) gene; a sequence from 93878120 to 95055725 of chromosome #13 (Genbank Accession No. NC_000013.10) for the GPC6 (glypican 6) gene; a sequence from 108115416 to 108507633 of chromosome #1 (Genbank Accession No. NC_000001.10) for the VAV3 (vav guanine nucleotide exchange factor 3) gene; a sequence from 390933 to 408871 of chromosome #6 (Genbank Accession No. NC_000006.11) for the IRF4 (interferon regulatory factor 4) gene; a sequence from 22223947 to 22528629 of chromosome #12 (Genbank Accession No. NC_000012.11) for the ST8SIA1 (ST8 alpha-N-acetyl-neuraminide alpha-2,8-sialyltransferase 1) gene; a sequence from 70512583 to 70655786 of chromosome #14 (Genbank Accession No. NC_000014.8) for the SLC8A3 (solute carrier family 8 member A3) gene; a sequence from 69242962 to 69702426 of chromosome #8 (Genbank Accession No. NC_000008.10) for the C8orf34 (chromosome 8 open reading frame 34) gene; a sequence from 43600469 to 43856442 of chromosome #11 for the AC068205.2 (AC068205.2) gene; a sequence from 23982579 to 24830965 of chromosome #10 (Genbank Accession No. NC_000010.10) for the KIAA1217 (KIAA1217) gene; a sequence from 20690141 to 21305005 of chromosome #11 (Genbank Accession No. NC_000011.9) for the NELL (neural EGFL like 1) gene; and a sequence from 137522139 to 138434806 of chromosome #2 (Genbank Accession No. NC_000002.11) for the THSD7B (thrombospondin type 1 domain containing 7B) gene.

In an embodiment, the agent capable of measuring the methylation level may be one selected from the group consisting of a compound modifying an unmethylated cytosine, a methylation-sensitive restriction enzyme, a primer capable of amplifying a fragment including a methylated base, a probe capable of hybridization with a fragment including a methylated base, a methylation-specific binding protein capable of binding to a methylated base, a methylation-specific binding antibody or aptamer, a methylation-sensitive restriction endonuclease, a sequencing primer, a sequencing by synthesis primer, and a sequencing by ligation primer.

The compound modifying an unmethylated cytosine may be a bisulfite, but is not limited thereto, and may be, for example, sodium bisulfite. Methods for detecting methylation by modifying an unmethylated ethylated cytosine residue using the bisulfite are well known in the art.

In addition, the methylation-sensitive restriction enzyme may be a restriction enzyme that specifically detects methylation of the CpG island, specifically, a restriction enzyme containing CG as a recognition site of the restriction enzyme. For example, the methylation-sensitive restriction enzyme may be SmaI, SacII, EagI, HpaII, MspI, BssHII, BstUI, NotI, or the like, but are not limited thereto. Cleavage by a restriction enzyme depends on the methylation or non-methylation at C of the restriction enzyme recognition site, and this may be detected by PCR or Southern Blot analysis. Methylation-sensitive restriction enzymes other than the above restriction enzymes are well known in the art.

The term "primer" refers to a nucleic acid sequence having a short free 3' hydroxyl group, capable of forming base pairs with a complementary template, and serving as a starting point of replication of a template strand. The primer may initiate DNA synthesis in the presence of a reagent for polymerization (i.e., DNA polymerase or reverse transcriptase) and four different nucleoside triphosphates in an appropriate buffer solution at an appropriate temperature. In addition, the primer is a sense or antisense nucleic acid having a nucleotide sequence of 7 to 50 nucleotides, and may incorporate an additional feature that does not change basic properties of the primer serving as an initiation point for DNA synthesis.

The primer according to an embodiment may be preferably designed in accordance with a sequence of the CpG island to be analyzed for occurrence of methylation, and may be a primer pair capable of specifically amplifying cytosine that is methylated and has not been changed by the bisulfite.

The term "probe" refers to a nucleic acid fragment such as an RNA or DNA including several to several hundreds of bases capable of binding specifically to a nucleic acid, and may be labeled to identify the presence or absence of a particular nucleic acid sequence. The probe may be prepared in the form of an oligo nucleotide probe, a single-stranded DNA probe, a double-stranded DNA probe, an RNA probe, or the like. Hybridization may be performed using a probe complementary to the polynucleotide of the gene according to an embodiment, and it may be assayed through whether or not hybridization occurs. Selection of a suitable probe and hybridization conditions may be modified based on those known in the art.

The term "antibody", as a term well known in the art, may refer to a specific protein molecule directed to an antigen site. The form of the antibody according to an embodiment is not particularly limited, and may include a polyclonal antibody, a monoclonal antibody, a part thereof as long as it has antigen-binding properties, and all immunoglobulin antibodies, and may also include special antibody such as humanized antibody. The antibody according to an embodiment may include not only a complete form having two full-length light chains and two full-length heavy chains but also a functional fragment of the antibody molecule. The functional fragment of the antibody molecule refers to a fragment containing at least an antigen-binding function, and may be for example, Fab, F(ab'), F(ab')2, Fv, and the like.

The term "diagnosis" refers to identification of the presence or features of a pathological condition. In view of the purpose of the present disclosure, the diagnosis may be identifying whether colorectal cancer is developed.

Another aspect provides a kit for diagnosing colorectal cancer comprising the composition. In the kit, the composition and diagnosis are as described above.

The kit may include a sectioned carrier containing a sample and an agent capable of measuring the methylation level of the gene. For example, the kit may include the sectioned carrier containing the sample and at least one container including a first container to containing an agent sensitively cleaving unmethylated cytosine, a second container containing a primer for amplifying a CpG-containing nucleic acid, and a third container containing means for detecting the presence of nucleic acids that is cleaved or not cleaved.

In an embodiment, the kit may be a nucleic acid chip for diagnosing colorectal cancer comprising a probe capable of hybridizing to a fragment including a methylated base of a gene selected from CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B. For example, the sample obtained from the subject or DNA isolated from the sample may be applied to the nucleic acid chip.

Another aspect provides a method of diagnosing colorectal cancer in a subject, the method comprising: measuring a methylation level of at least one gene selected from the group consisting of CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B in a biological sample obtained from the subject; and comparing the measured methylation level of the gene with a methylation level of a normal control. In the method, the methylation, methylation level, measuring of the methylation level, and diagnosis are as described above.

The term "subject" may refer to a mammal including humans, for example, may be an experimental animals showing pathological condition of cancer including colorectal cancer, such as monkeys and rodents. In an embodiment, the subject may be a human.

The term "biological sample" may refer to a sample obtained from an individual. The biological sample may encompass a wide range of all biological samples obtained from an individuals, body fluids, cell lines, tissue cultures, and the like, depending on the type of analysis to be performed, for example, blood, serum, plasma, saliva, feces, urine, cells, tissue, biopsies, paraffin tissue, and fine needle aspiration biopsy sample. In an embodiment, the biological sample may be blood, particularly, plasma isolated from the blood. Methods for obtaining body fluids and/or biopsy samples from mammals including humans are well known in the art.

In an embodiment, the measuring of the methylation level of the gene may be performed by a method selected from the group consisting of PCR, methylation-specific PCR, real-time methylation-specific PCR, MethyLight PCR, MethyLight digital PCR, EpiTYPER, PCR using a methylation DNA-specific binding protein, quantitative PCR, DNA chip, pyrosequencing, bisulfite sequencing, Southern blotting, restriction landmark genomic scanning (RLGS), SNuPE, CpG island microarray, single-nucleotide primer extension, a combined bisulfite-restriction analysis (COBRA), methylated-CpG island recovery assay (MIRA), and mass spectrometry, without being limited thereto.

In an embodiment, the method may further include determining that the subject has a high probability of developing colorectal cancer or has colorectal cancer when the methylation level of the gene measured in the biological sample obtained from the subject is different from, or particularly is increased when compared to, the methylation level of the normal control. The term "increased methylation level" may refer to that the methylation level of the gene in the sample of the subject is significantly increased to a measurable degree as compared to a control group, for example increased by about 1.1 times or more, e.g., by 1.1 times to 10 times, by 1.1 times, 1.5 times, 2 times, 3 times, 4 times, 5 times, 6 times, 7 times, 8 times, 9 times, or 10 times or more.

In an embodiment, the method may further comprise administering a therapeutic agent such as an anti-cancer drug or a substance for alleviation, when the subject is determined to have a high probability of developing colorectal cancer or has colorectal cancer. The administration may be performed by oral administration or parenteral administration. The anti-cancer drug may be a chemotherapy anti-cancer drug, for example, fluoropyrimidine-based drugs such as 5-fluorouracil (5-FU) and capecitabine, irinotecan, oxaliplatin, and drugs for targeted treatment such as bevacizumab, cetuximab, regorafenib, and aflibercept, but is not limited thereto.

In an embodiment, the measuring of the methylation level may be performed by measuring methylation levels of two or more genes selected from the group consisting of CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B in the biological sample obtained from the subject. That is, the method may be a diagnosis using a specific combination of the genes, and the accuracy of the diagnosis may be improved by using a combination of the biomarkers compared to using a single biomarker. In an embodiment, the measuring of the methylation level may be performed by measuring methylation levels of 2, 3, 4, 5, 6, 7, 8, 9, 10, 11, 12, 13, 14, 15, 16 or more genes among the genes. For example, the diagnosis may be performed by using combinations of CFL1 and FAM19A2, CFL1 and LTBP4, CFL1 and VIM, CFL1 and RNF220, CFL1 and KCNQ5, CFL1 and GPC6, CFL1 and VAV3, CFL1 and IRF4, CFL1 and ST8SIA1, CFL1 and SLC8A3, CFL1 and C8orf34, CFL1 and AC068205.2, CFL1 and KIAA1217, CFL1 and NELL1, CFL1 and THSD7B, FAM19A2 and LTBP4, FAM19A2 and VIM, FAM and RNF220, FAM19A2 and KCNQ5, FAM and GPC6, FAM19A2 and VAV3, FAM19A2 and IRF4, FAM19A2 and ST8SIA1, FAM19A2 and SLC8A3, FAM19A2 and C8orf34, FAM19A2 and AC068205.2, FAM19A2 and KIAA1217, FAM19A2 and NELL1, FAM19A2 and THSD7B, LTBP4 and VIM, LTBP4 and RNF220, LTBP4 and KCNQ5, LTBP4 and GPC6, LTBP4 and VAV3, LTBP4 and IRF4, LTBP4 and ST8SIA1, LTBP4 and SLC8A3, LTBP4 and C8orf34, LTBP4 and AC068205.2, LTBP4 and KIAA1217, LTBP4 and NEW, LTBP4 and THSD7B, VIM and RNF220, VIM and KCNQ5, VIM and GPC6, VIM and VAV3, VIM and IRF4, VIM and ST8SIA1, VIM and SLC8A3, VIM and C8orf34, VIM and AC068205.2, VIM and KIAA1217, VIM and NELL1, VIM and THSD7B, RNF220 and KCNQ5, RNF220 and GPC6, RNF220 and VAV3, RNF220 and IRF4, RNF220 and ST8SIA1, RNF220 and SLC8A3, RNF220 and C8orf34, RNF220 and AC068205.2, RNF220 and KIAA1217, RNF220 and NELL1, RNF220 and THSD7B, KCNQ5 and GPC6, KCNQ5 and VAV3, KCNQ5 and IRF4, KCNQ5 and ST8SIA1, KCNQ5 and SLC8A3, KCNQ5 and C8orf34, KCNQ5 and AC068205.2, KCNQ5 and KIAA1217, KCNQ5 and NELL1, KCNQ5 and THSD7B, GPC6 and VAV3, GPC6 and IRF4, GPC6 and ST8SIA1, GPC6 and SLC8A3, GPC6 and C8orf34, GPC6 and AC068205.2, GPC6 and KIAA1217, GPC6 and NELL1, GPC6 and THSD7B, VAV3 and IRF4, VAV3 and ST8SIA1 VAV3 and SLC8A3, VAV3 and C8orf34, VAV3 and AC068205.2, VAV3 and KIAA1217, VAV3 and NELL1, VAV3 and THSD7B, IRF4 and ST8SIA1, IRF4 and SLC8A3, IRF4 and C8orf34, IRF4 and AC068205.2, IRF4 and KIAA1217, IRF4 and NELL1, IRF4 and THSD7B, ST8SIA1 and SLC8A3, ST8SIA1 and C8orf34, ST8SIA1 and AC068205.2, ST8SIA1 and KIAA1217, ST8SIA1 and NELL1, ST8SIA1 and THSD7B, SLC8A3 and C8orf34, SLC8A3 and AC068205.2, SLC8A3 and KIAA1217, SLC8A3 and NELL1, SLC8A3 and THSD7B, C8orf34 and AC068205.2, C8orf34 and KIAA1217, C8orf34 and NELL1, C8orf34 and THSD7B, AC068205.2 and KIAA1217, AC068205.2 and NELL1, AC068205.2 and THSD7B, KIAA1217 and NELL1, KIAA1217 and THSD7B, or NELL1 and THSD7B.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to the following examples However, the following examples are merely presented to exemplify the present disclosure, and the scope of the present disclosure is not limited thereto.

Example 1

Selection of Methylation Marker for Diagnosis of Colorectal Cancer (1.1) Preparation of Sample In order to derive genes whose methylation level changes specifically in colorectal cancer tissue, fresh frozen tissue of 100 patients with colorectal cancer stored in the biobank of the Samsung Medical Center (Seoul, Korea) was obtained and samples of colorectal cancer tissue, normal tissue around the cancer tissue, and blood tissue samples were collected.

Particularly, the frozen tissue was crushed using liquid nitrogen and completely degraded by adding a lysis buffer thereto. After centrifugation, only a supernatant was collected, and genomic DNA was extracted from each sample using a column-based DNA extraction method (PureLink™ Genomic DNA Mini Kit, Invitrogen).

(1.2) Bisulfite Sequencing Data Generation

Bisulfite sequencing was performed on the genomic DNA obtained in Example (1.1) to generate methylation data.

Particularly, after cleaving 300 ng of genomic DNA into about 200 bp using covaries, a methylated adaptor applicable to an illumine sequencer was attached to the end of the cleaved DNA fragment to prepare a whole genome library. For the prepared library, only a portion of the genome to be observed among the entire genome was selected using a Human Methyl-Seq Capture Library (Cat. #5190-4662) of Agilent, and the selected portion was treated with bisulfite using an EZ DNA methylation-Gold kit (Zymo Research, USA). When genomic DNA is treated with bisulfite, a methylated cytosine in the 5'-CpG-3' site of the DNA base sequence is maintained as it is, but an unmethylated cytosine is converted into uracil, and thus the methylation level can be measured. After converting uracil of the DNA treated with bisulfite back into thymine using PCR, sequencing was performed to obtain methylation data.

(1.3) Selection of Gene Marker Via Statistical Test

In order to derive genes whose methylation level changes specifically in colorectal cancer tissue from the bisulfite sequencing data obtained in Example (1.2), the colorectal cancer tissue samples were used as experimental groups, and a normal tissue sample around the cancer tissue and a blood tissue sample were used as controls, and genes exhibiting a large difference in methylation level between the experimental groups and the controls were selected through statistical tests.

First, the difference in methylation level between the experimental groups and the controls was derived at the CpG site level from the bisulfite sequencing data obtained in Example (1.2). The p-value was derived by testing the ratio of methylated sites between the experimental group and the control group by t-test. In order to comprehensively test the information of various CpG sites in one gene, statistical tests were performed on the basis of gene unit by integrating the significance of the CpG site unit into the significance of the gene unit using Empirical Brown's method (EBM) (Poole, William, et al., Bioinformatics, 2016). Since it is known from the documents of the related art that closer CpG sites have a higher correlation, the method was selected to consider the correlation. In the comparison tests between the experimental group (tumor) and the two control groups (Normal and Blood), the genes that was in the top 100 ranking in both tests were selected as final marker based on the p-value. The following Table 1 shows p-values of 16 gene markers derived as a result of the comparison test between the experimental group (tumor) and the two control groups (Normal and Blood). The following Table 2 shows the region of the CpG site of the gene used in the comparison test between the experimental group (tumor) and the control group (Blood) in Table 1. The following Table 3 shows the region of CpG site of the gene used in the comparison test between the experimental group (tumor) and the control group (Normal) in Table 1.

TABLE 1

| Gene | no. of CpG sites | mean Tumor | mean Blood | difference ($\Delta\beta$) | Combined P-value | Gene |
|---|---|---|---|---|---|---|
| CFL1 | 144 | 0.380756892 | 0.346162781 | 0.034594111 | <4.80E−289 | CFL1 |
| FAM19A2 | 172 | 0.468323665 | 0.229727036 | 0.23859663 | <4.80E−289 | FAM19A2 |
| LTBP4 | 235 | 0.333554142 | 0.315485254 | 0.018068888 | <4.80E−289 | LTBP4 |
| VIM | 160 | 0.274581426 | 0.102204987 | 0.172376439 | <4.80E−289 | VIM |
| RNF220 | 481 | 0.45415005 | 0.366477944 | 0.087672105 | 4.79E−289 | RNF220 |
| KCNQ5 | 185 | 0.504692771 | 0.334217467 | 0.170475304 | 7.73E−276 | KCNQ5 |
| GPC6 | 257 | 0.473563441 | 0.352574178 | 0.120989263 | 4.89E−271 | GPC6 |
| VAV3 | 108 | 0.363354079 | 0.324919696 | 0.038434383 | 8.05E−269 | VAV3 |
| IRF4 | 250 | 0.473345642 | 0.102998256 | 0.370347385 | 1.34E−229 | IRF4 |
| ST8SIA1 | 204 | 0.327833014 | 0.214223263 | 0.113609751 | 4.21E−247 | ST8SIA1 |
| SLC8A3 | 165 | 0.375516551 | 0.249861985 | 0.125654566 | 2.56E−236 | SLC8A3 |
| C8orf34 | 145 | 0.483557247 | 0.268824903 | 0.214732344 | 1.23E−241 | C*orf34 |
| AC068205.2 | 201 | 0.373859922 | 0.176243055 | 0.197616867 | 2.33E−231 | AC068205.2 |
| KIAA1217 | 285 | 0.451313377 | 0.391203381 | 0.060109997 | <4.80E−289 | KIAA1217 |
| NELL1 | 187 | 0.449607915 | 0.244476671 | 0.205131244 | 2.83E−273 | NELL1 |
| THSD78 | 149 | 0.468474161 | 0.266869045 | 0.201605116 | 2.02E−248 | THSD7B |

TABLE 1-continued

| Gene | no. of CpG sites | mean Tumor | mean Normal | difference (Δβ) | Combined P-value |
|---|---|---|---|---|---|
| CFL1 | 134 | 0.44345697 | 0.300279469 | 0.1431775 | 1.21E−283 |
| FAM19A2 | 150 | 0.471903035 | 0.348730633 | 0.123172403 | 4.18E−153 |
| LTBP4 | 174 | 0.316116016 | 0.199062307 | 0.117053709 | 1.71E−138 |
| VIM | 148 | 0.267321471 | 0.086599746 | 0.180721725 | 1.88E−187 |
| RNF220 | 361 | 0.420734027 | 0.269753729 | 0.150980298 | 3.89E−163 |
| KCNQ5 | 180 | 0.507863437 | 0.318686025 | 0.189177412 | 1.88E−190 |
| GPC6 | 248 | 0.465026578 | 0.292952847 | 0.172073731 | 1.37E−298 |
| VAV3 | 97 | 0.339323327 | 0.275296644 | 0.064025683 | 9.77E−148 |
| IRF4 | 245 | 0.463653657 | 0.136505138 | 0.327148518 | 1.48E−186 |
| ST8SIA1 | 198 | 0.301986066 | 0.21055742 | 0.091428646 | 3.58E−189 |
| SLC8A3 | 133 | 0.381386817 | 0.190188367 | 0.19119845 | 3.03E−156 |
| C8orf34 | 144 | 0.47474466 | 0.234076477 | 0.240668183 | 1.03E−249 |
| AC068205.2 | 188 | 0.35337365 | 0.147786827 | 0.205568823 | 6.92E−140 |
| KIAA1217 | 236 | 0.449009671 | 0.279570532 | 0.169439139 | 4.62E−163 |
| NELL1 | 180 | 0.454625197 | 0.249580138 | 0.205045059 | 5.11E−169 |
| THSD78 | 145 | 0.476299242 | 0.283470297 | 0.192828945 | 2.34E−198 |

TABLE 2

| Methylation pattern in the Tumor vs. Blood | Gene | No. of CpG sites | Chromosomal location of CpG sites | |
|---|---|---|---|---|
| Hyper | CFL1 | 144 | chr11 | 65589615 65629481 |
| | FAM19A2 | 172 | chr12 | 62102663 62661012 |
| | LTBP4 | 235 | chr19 | 41098689 41135467 |
| | VIM | 160 | chr10 | 17270300 17277761 |
| | RNF220 | 481 | chr1 | 44870219 45117290 |
| | KCNQ5 | 185 | chr6 | 73331531 73907779 |
| | GPC6 | 257 | chr13 | 93878120 95055725 |
| | VAV3 | 108 | chr1 | 108115416 108507633 |
| | IRF4 | 250 | chr6 | 390933 408871 |
| | ST8SIA1 | 204 | chr12 | 22223947 22528629 |
| | SLC8A3 | 165 | chr14 | 70512583 70655786 |
| | C8orf34 | 145 | chr8 | 69242962 69702426 |
| | AC068205.2 | 201 | chr11 | 43600469 43856336 |
| | KIAA1217 | 285 | chr10 | 23982579 24830965 |
| | NELL1 | 187 | chr11 | 20690141 21305005 |
| | THSD7B | 149 | chr2 | 137522139 138434806 |

TABLE 3

| Methylation pattern in the Tumor vs. Normal | Gene | No. of CpG sites | Chromosomal location of CpG sites | |
|---|---|---|---|---|
| Hyper | CFL1 | 134 | chr11 | 65589615 65629437 |
| | FAM19A2 | 150 | chr12 | 62102663 62654401 |
| | LTBP4 | 174 | chr19 | 41100577 41135447 |
| | VIM | 148 | chr10 | 17270300 17277411 |
| | RNF220 | 361 | chr1 | 44870688 45117290 |
| | KCNQ5 | 180 | chr6 | 73331531 73907779 |
| | GPC6 | 248 | chr13 | 93878120 95055725 |
| | VAV3 | 97 | chr1 | 108115416 108507633 |
| | IRF4 | 245 | chr6 | 390933 408871 |
| | ST8SIA1 | 198 | chr12 | 22224195 22528629 |
| | SLC8A3 | 133 | chr14 | 70514246 70655786 |
| | C8orf34 | 144 | chr8 | 69242962 69702426 |
| | AC068205.2 | 188 | chr11 | 43600469 43856442 |
| | KIAA1217 | 236 | chr10 | 23982579 24830928 |
| | NELL1 | 180 | chr11 | 20690141 21305005 |
| | THSD7B | 145 | chr2 | 137522139 138434806 |

As shown in Tables 1 to 3, as a result of evaluating the significance of the difference in methylation level between the experimental group (Tumor) and two control groups (Normal and Blood) by integrating them in a gene unit, a total of 16 genes (CFL1, FAM19A2, LTBP4, VIM, RNF220, KCNQ5, GPC6, VAV3, IRF4, ST8SIA1, SLC8A3, C8orf34, AC068205.2, KIAA1217, NELL1, and THSD7B) were found to have p-values in the top 100 ranking in both comparison tests with the two control groups. Therefore, the genes were finally selected as colorectal cancer-specific methylation markers. In addition, in all of the above genes, the experimental group (Tumor) was found to be hypermethylated compared to the two control groups (Normal and Blood), suggesting that colorectal cancer can be diagnosed by identifying hypermethylation of the CpG sites of the genes.

Since the gene marker according to an embodiment exhibits a specific methylation pattern in colorectal cancer tissue, it can be usefully used as a methylation marker for diagnosing colorectal cancer, thereby increasing the cure rate of colorectal cancer by early diagnosis and treatment of colorectal cancer.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of diagnosing and treating colorectal cancer in a subject, the method comprising:
    measuring a methylation level of a CpG site of CFL1 and FAM19A2 in a biological sample obtained from the subject;
    comparing the measured methylation level of CFL1 and FAM19A2 with a methylation level of a normal control;
    detecting an increased methylation of CFL1 and FAM19A2 compared to a normal control;
    determining a high probability of developing colorectal cancer in the subject that has an increased methylation level of CFL1 and FAM19A2; and
    administering a therapeutic agent to the determined subject, wherein the therapeutic agent is selected from the group consisting of 5-fluorouracil, capecitabine, irinotecan, oxaliplatin, bevacizumab, cetuximab, regorafenib, and aflibercept.

2. The method of claim 1, wherein the measuring of the methylation level is performed using an agent selected from the group consisting of a compound modifying an unmethylated cytosine, a methylation-sensitive restriction enzyme, a primer capable of amplifying a fragment including a methylated base, a probe capable of hybridization with a fragment including a methylated base, a methylation-specific binding protein capable of binding to a methylated base, a methylation-specific binding antibody or aptamer, a methylation-sensitive restriction endonuclease, a sequencing primer, a sequencing-by-synthesis primer, and a sequencing-by-ligation primer.

3. The method of claim 1, wherein the measuring of the methylation level of the gene is performed by a method selected from the group consisting of PCR, methylation-specific PCR, real-time methylation-specific PCR, MethyLight PCR, MethyLight digital PCR, PCR using a methylation DNA-specific binding protein, quantitative PCR, DNA chip, pyrosequencing, bisulfate sequencing, Southern blotting, restriction landmark genomic scanning (RLGS), CpG island microarray, single-nucleotide primer extension, combined bisulfate-restriction analysis (COBRA), methylated-CpG island recovery assay (MIRA), and mass spectrometry.

4. The method of claim 1, wherein the biological sample is selected from the group consisting of tissue, cells, blood, serum, plasma, saliva, feces, and urine.

* * * * *